United States Patent [19]

Kaneko et al.

[11] Patent Number: 5,344,400
[45] Date of Patent: Sep. 6, 1994

[54] BALLOON CATHETERS CONTAINING MOLDED POLYARYLENESULFIDE MATERIAL

[75] Inventors: Takashi Kaneko; Toshinobu Ishida; Akira Mochizuki, all of Ashigarakami, Japan

[73] Assignee: Terumo Kabushiki Kaisha, Tokyo, Japan

[21] Appl. No.: 46,262

[22] Filed: Apr. 6, 1993

[30] Foreign Application Priority Data

Apr. 6, 1992 [JP] Japan ................................. 4-084172

[51] Int. Cl.⁵ .............................................. A61M 29/02
[52] U.S. Cl. ........................................ 604/96; 606/192
[58] Field of Search .............................. 604/96–103; 606/192–196; 600/18

[56] References Cited

U.S. PATENT DOCUMENTS

| | | |
|---|---|---|
| 3,948,823 | 4/1976 | Lee et al. .................... 260/2.5 M |
| 3,951,789 | 4/1976 | Lee et al. ........................ 210/22 C |
| 4,093,484 | 6/1978 | Harrison et al. . |
| 4,154,244 | 5/1979 | Becker et al. . |
| 4,254,774 | 3/1981 | Boretos . |
| 4,906,244 | 3/1990 | Pinchuk et al. . |
| 5,108,415 | 4/1992 | Pinchuk et al. . |

FOREIGN PATENT DOCUMENTS 349640 1/1990 European Pat. Off. .

*Primary Examiner*—John D. Yasko
*Assistant Examiner*—Adam J. Cermak
*Attorney, Agent, or Firm*—Burns, Doane, Swecker & Mathis

[57] ABSTRACT

A balloon catheter having a balloon which is produced by molding polyarylenesulfide or an alloy thereof wherein polyarylenesulfide is a main constituent, and the balloon is provided with excellent dimensional stability as well as sufficient softness and flexibility, leading to an improved trackability of the catheter to reach the target lesion.

7 Claims, 1 Drawing Sheet

BALLOON CATHETERS CONTAINING MOLDED POLYARYLENESULFIDE MATERIAL

BACKGROUND OF THE INVENTION

This invention relates to a balloon catheter having a novel balloon.

A balloon catheter having an inflatable balloon secured at its distal end has been applied for various cavities in a living body including a blood vessel. Utility of the balloon catheter is increasing in various medical fields.

Of the balloon catheters mentioned above, a blood vessel-dilating catheter is employed in percutaneous transluminal coronary angioplasty (PTCA) to dilate a stenosis or a narrowing in a blood vessel such as coronary artery or percutaneous transluminal angioplasty (PTA) to dilate a stenosis or a narrowing in a peripheral blood vessel. In PTCA, femoral artery is secured, for example, by Serdinger method; the distal end of a guiding catheter is introduced into the thus secured femoral artery and advanced through the lumen of the artery until it reaches the entry of the target coronary artery; a blood vessel-dilating catheter is introduced into the lumen of the guiding catheter to locate the balloon at the narrowing in the blood vessel; and a blood vessel-dilating fluid is introduced into the lumen of the blood vessel-dilating catheter to inflate the balloon to thereby dilate the narrowing in the blood vessel.

Such a blood vessel-dilating catheter is required to have a trackability so that the blood vessel-dilating catheter can smoothly advance through the lumen of the guiding catheter along the tortuous blood vessel to reach the lesion site. The balloon is required to have a sufficient dimensional stability as well as excellent strength and flexibility so as to avoid excess dilation of the narrowing of the blood vessel.

Typical balloons for balloon catheters are disclosed in U.S. Pat. No. 4,093,484; 4,154,244; 4,254,774; 4,906,244; and 5,108,415; and PCT Application No. JP88/00202.

The balloons described in these patents and patent application comprise for example mixture of an ethylene-butylene-styrene block copolymer and a low molecular weight polystyrene having polypropylene optionally added thereto; a composition similar to the one just mentioned wherein butadiene or isoprene is used instead of the ethylene and the butylene; polyvinyl chloride; polyurethane; a polyester copolymer; a thermoplastic rubber; a silicone-polycarbonate copolymer; an ethylene-vinyl acetate copolymer; biaxially oriented Nylon 12; biaxially oriented polyethylene terephthalate; polyethylene; and a crosslinked ethylene-vinyl acetate copolymer.

The material particularly used for the balloons of the blood vessel-dilating catheters include polyvinyl chloride (hereinafter abbreviated as PVC), polyethylene (hereinafter abbreviated as PE), biaxially oriented Nylon 12 (hereinafter abbreviated as N12), and biaxially oriented polyethylene terephthalate (hereinafter abbreviated as PET).

Among these, aliphatic high polymers such as PE, PVC and N12 are highly flexible, realizing a sufficient trackability. These materials, however, are insufficient in their strength to detract from dimensional stability.

PET, on the other hand, has excellent strength and dimensional stability. PET, however, has an excessively high modulus of elasticity due to crystallization caused by the biaxial orientation, and therefore, is inferior in impact strength, tear resistance and flexibility, leading to poor trackability of the catheter.

Furthermore, PET is poor in coating adaptability, adhesibility, and heat sealability and results in balloon catheters comprising inadequate operativity and workability. In addition, PET inherently lacks antithrombotic properties, and it would be quite difficult to subject the PET to various treatments to impart biocompatibility, in particular, blood compatibility.

Since medical instruments are used directly in human bodies, they need to be sterilized and pasteurized for safety. Since prior art catheter balloons made of PE, PVC, N12 and PET are inferior in heat resistance and radiation resistance, they cannot be subjected to autoclave sterilization and γ-ray sterilization. Therefore, they have been subjected to sterilization in an atmosphere of an ethylene oxide gas (hereinafter abbreviated as EOG). However, after sterilization EOG remains on the product. Moreover, since EOG causes hemolysis, it is necessary to remove the EOG, which removal process takes about a week. This results in safety and productivity problems.

The present invention has been achieved in view of the above-described situation. An object of the present invention is to provide a balloon for a balloon catheter wherein the softness and the flexibility are improved without compromising the dimensional stability. Another object of the present invention is to provide a balloon for a blood vessel-dilating catheter wherein the modulus of elasticity is reduced to prevent an injury of the blood vessel inner surface.

According to the present invention, there is provided a balloon for a balloon catheter fabricated by molding polyarylenesulfide (hereinafter abbreviated as PAS) or a polymer alloy thereof comprising PAS as one of its components.

Also, according to the present invention, there is provided a balloon for a balloon catheter fabricated by multi-layered extrusion molding of PAS and olefin.

The PAS may preferably be at least one selected from the group consisting of polyphenylenesulfide (hereinafter abbreviated as PPS), polythioether ketone, polythioether thioether ketone, polythioether ketone ketone, polyether thioether, polythioether sulfone, polybiphenylene sulfide and polynaphthalene sulfide.

The PAS may preferably be a high molecular weight PPS.

The balloon preferably has a calculated modulus of elasticity of from 70 to 200 kg/mm$^2$.

The balloon may preferably has a burst pressure of at least 10 kg/cm$^2$.

The balloon film being fabricated by PAS or a polymer alloy thereof comprising PAS as one of its components may preferably be oriented biaxially.

DETAILED DESCRIPTION OF THE INVENTION

Figure 1:
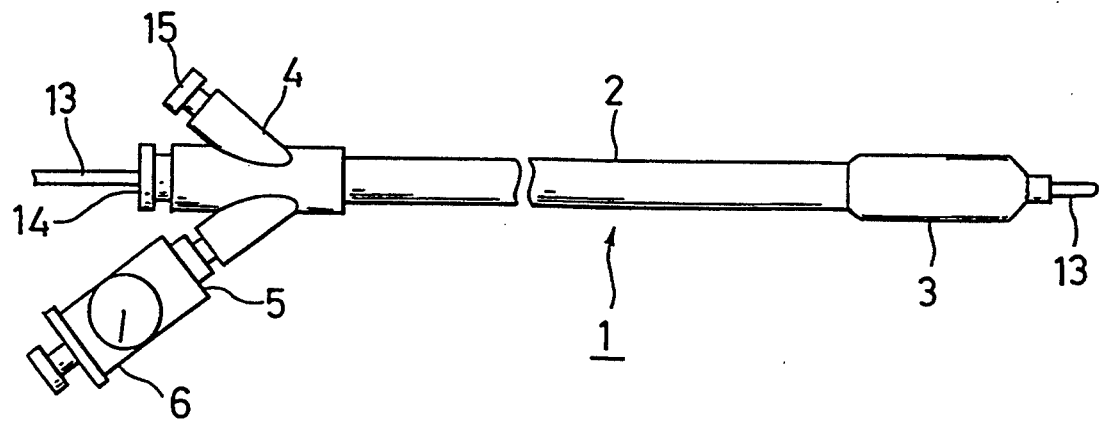
FIG. 1 is a schematic diagram of the configuration of a triple tubular blood vessel-dilating catheter provided with a balloon for experimentation according to an embodiment of the present invention.

PET, as described above, has a high strength, a high modulus of elasticity and a good dimensional stability, although it is poor in flexibility and water absorption. Therefore, when it is not perfectly dried, the molecular weight is reduced at the time of molding, resulting in poor strength and orientation and rendering the balloon molding difficult. On the other hand, aliphatic polymers such as PE, PVC and N12 are highly flexible, and the resulting blood vessel-dilating catheter may have a good trackability. Such aliphatic polymers, however, are poor in strength and dimensional stability, and also, suffer from decrease in their strength and dimensional alteration caused by temperature variations and water impregnation.

In contrast, the balloon used in the balloon catheter (hereinafter simply referred to as balloon) of the present invention comprises polyarylenesulfide which has an excellent dimensional stability, or polyphenylenesulfide, a polymer alloy prepared by copolymerizing or mixing polyarylenesulfide with a softener for denaturation. A balloon having both excellent dimensional stability and high flexibility is thereby provided.

Such a balloon having excellent dimensional stability as well as high flexibility may be introduced into the blood vessel with little impact against the blood vessel inner surface to prevent the blood vessel inner surface from being injured.

The reduced modulus of elasticity results in a highly flexible, soft balloon which may be easily folded to a small size. Hard materials like PET having a high modulus of elasticity are difficult to fold into a small size due to rigid folds formed upon folding.

On the other hand, the balloon of the present invention can be folded to a small size with no rigid fold being formed by folding owing to its flexibility and softness.

The balloon of the present invention has a good trackability to enable the catheter to reach the target lesion. More illustratively, the trackability of the catheter depends not only the foldability of the balloon to a small size but also on the flexibility of the folded balloon, shell. The balloon formed of PET is poor in the flexibility of the shell to result in an inferior trackability of the catheter provided with the PET balloon. In contrast, the shell of the balloon of the present invention is soft and flexible to realize a good trackability of the catheter.

Since the balloon of the present invention has higher heat resistance than the balloon of PET due to the properties of the material, it is not deformed after it is subjected to plasma treatment (corona treatment). Therefore, one has the option to improve adhesibility by means of denaturation making use of plasma treatment as required. Moreover because the surface treated balloon of the present invention is superior in adhesion strength to the PET balloon, the balloon is not peeled off the catheter body during its storage or use. In addition, since the balloon of the present invention has good compatibility with other resins as well as good coating adaptability, the balloon may be surface treated with various agents and resin coatings to realize sustained effects of the treatment.

For example, the balloon may have its exterior surface treated with various antithrombotic materials and agents to impart the balloon with a high blood compatibility for a prolonged period. The surface of the balloon may be subjected to other surface treatments for other purposes including smooth passage of the balloon through the lumen of the blood vessel filled with viscous blood, and prevention of the blood vessel interior surface from being injured by the traffic of the balloon.

Moreover, since the balloon of the present invention has excellent heat resistance and an extremely small coefficient of water absorption due to the properties inherent to the material thereof, it can undergo autoclave sterilization. Conventional materials such as PET have low heat resistance and are water absorptive, and accordingly, deformation and lowered strength of the balloon occur after it undergoes general autoclave sterilization in an atmosphere of aqueous vapor at a temperature of 121° C. and a pressure of 1.1 $kg/cm^2$ for 20 minutes. Even under such severe sterilization conditions, the balloon of the present invention is not deformed and does not suffer from lowered strength after a repetition of sterilization operation. In addition, since the balloon of the present invention has radiation resistance due to the properties inherent to the material thereof, it can undergo $\gamma$-ray sterilization.

Therefore, the balloon of the present invention can undergo autoclave sterilization and $\gamma$-ray sterilization other than sterilization making use of ethylene oxide gas which may cause hemolysis and is preferably used as a balloon for a blood vessel-dilating catheter which is contacted directly to blood.

Although the above-mentioned aliphatic polymers such as PE, PVC and N12 are flexible, they have low calculated modulus of elasticity and low burst pressure. On the other hand, the balloon made from the above-mentioned PET has a high burst pressure. However, once the PET balloon undergo bursting, it disrupts into numerous small pieces or debris which are quite difficult to recollect. In contrast, the balloon of the present invention has a high burst pressure and would not burst even when a pressure of about 10 atmosphere is applied for expansion of the balloon, and even when the balloon should burst, it tears in a wadding configuration to enable a safe recollect.

The balloon used in the balloon catheter of the present invention comprises as a construction material thereof either polyarylenesulfide having a good dimensional stability, or a polyarylenesulfide-based polymer alloy modified by blending polyarylenesulfide as a constituent or a main constituent with another resin providing flexibility (elasticity) or copolymerizing with another component providing softness. Ratio of the components may be adjusted to realize desired properties including a calculated modulus of elasticity in the range of from 70 to 200 $kg/mm^2$.

The term polyarylenesulfide used herein designates a sulfur-containing aromatic polymer typified by polyphenylenesulfide (hereinafter abbreviated as PPS). Other aromatic polymers include polythioether ketone, polythioether thioether ketone, polythioether ketone ketone, polyether thioether, polythioether sulfone, polybiphenylene-sulfide and polynaphthalenesulfide. The polyarylenesulfide of this invention have an aromatic compound as a repeating unit and a sulfur as a coupling component. Among these, polyphenylenesulfide is particularly preferred.

The Polyarylenesulfide may have a polymerization degree of approximately 50 to 5000, and most preferably approximately 100 to 3,000, and an average molecular weight of approximately 5,000 to 500,000, and most preferably approximately 10,000 to 300,000. The crystallization degree ranges from 0 to 60, and most preferably from 5 to 40.

In the present invention, such polyarylenesulfide as described above may be used either alone or as a main component in a polymer alloy wherein the polyarylenesulfide is blended with a resin providing flexibility (elasticity) to the balloon or copolymerized with another component providing softness. Illustrative polymer alloys include polymer blends, graft copolymers, block copolymers (micro phase separation structure) and random copolymers. An alloying agent, a compatibilizing agent or a stabilizing agent may optionally be employed in alloying the polyarylenesulfide.

Exemplary alloying resins to be blended with the polyarylenesulfide for denaturation may be used singularly or in combination and include thermoplastic resins such as modified polyolefin, fluororesin, polyethylene, polyamide, polyester, polystyrene, polycarbonate, polyphenylene oxide, polyether ketone and polyether imide. The blends of polyarylenesulfides themselves may also be used. Among these, PPS-based polymer blends are preferable in view of their availability and sufficient workability. Further, the polymer blend of a high molecular weight linear type PPS and polystyrene is most preferable in view of its improved flexibility and compatibility.

The resin providing such flexibility may comprise up to 50% by weight, most preferably from 0 to 40% by weight of the polymer alloy. When the flexible resin component comprises more than 50% by weight, the resulting balloon would be too poor in its modulus of elasticity and strength leading to insufficient dimensional stability.

The copolymerization of polyarylenesulfide for denaturation may provide for a decrease in crystallinity by means of random or block copolymerization of polyarylenesulfides themselves or block copolymerization with an elastomer component. The copolymers of PPS prepared by random copolymerization or block copolymerization with a meta-oriented polyarylenesulfide component is a preferred polymer in view of its availability and good workability and preferably comprises less than 50% by weight of the meta component, and most preferably from 0 to 30% by weight of the component. To lower the crystallinity and the modulus of elasticity and maintain the dimensional stability of the PPS, it is preferred that crystallinity remains in the PPS. When the content of the meta component is more than 50% by weight, the PPS is made non-crystalline by random copolymerization, whereby the preparing of the balloon by means of biaxial orientation is difficult.

The balloon of the present invention may be secured to the catheter body, which will typically comprise a resin material such as polyvinyl chloride and polyethylene, by thermal fusion using a suitable heating means or with an adhesive or a solvent such as epoxy resin or cyanoacrylate adhesive. Since the balloon of the present invention has an excellent heat resistance owing to the properties of the resin material, it is not deformed by corona treatment. Therefore, it is possible to improve compatibility (adhesibility) with the balloon catheter body, particularly adhesion strength, by subjecting the balloon to corona treatment before adhesion. Therefore, the balloon of the present invention is advantageous in industrial processes and may be safely stored and used with no risk of the balloon from being peeled off the catheter body.

The balloon of the present invention is produced by molding, preferably biaxially orienting, the above-described polyarylenesulfide or a polymer alloy thereof wherein the polyarylenesulfide is a main constituent.

In an exemplary process for producing the balloon of the present invention, a tube or tubular body is fabricated from the above-mentioned polyarylenesulfide or the alloy thereof wherein the polyarylenesulfide is a main constituent; and the thus produced tube is axially oriented by such means as elongation or drawing. The axial orientation may preferably be carried out at an elevated temperature of, for example, from 45 to 150° C.

The thus axially oriented tube may have a length larger than its preorientation length by a factor of about 1.5 to 5.

Next, a mold having a cavity of a configuration corresponding to the balloon in its inflated state is placed over the axially oriented tube at approximately central position in its axial direction. The mold is then heated to a temperature of, for example, from 45 to 150° C. to heat the tube. The tube is inflated in its radial direction at the heated portion by applying an elevated pressure. The radius of the tube after the inflation may be about two to eight times larger than the radius of the tube before the inflation. The thus obtained balloon may have a thickness of from 5 to 50 $\mu$m, and more preferably from 5 to 30 $\mu$m.

The heated, pressurized conditions of the tube as described above are maintained for a certain period, for example, one second to five minutes, and then, the tube is allowed to cool to approximately room temperature while the elevated pressure within the tube is maintained. The tube is thus oriented in its radial direction to form the desired balloon configuration. It is to be noted that the balloon may be subjected to repeated cycles of heat application and cooling to thereby remove the strain of the balloon.

After the cooling of the tube to approximately room temperature, the pressure is reduced to normal pressure, the mold is removed, and the balloon is trimmed to produce the balloon of the present invention.

Moreover, the balloon of the present invention may also be produced by preparing a tube by means of multilayer extrusion molding of PAS and an olefin and biaxially orientating the tube in the same manner as described above. Almost all polyolefins used for medical application can be used as the olefin used herein. The olefin may preferably be polypropylene, polyethylene, an ethylene-propylene copolymer, an ethylene-vinyl acetate copolymer, modified polyolefins such as modified polyethylene and modified polypropylene and olefin-based elastomers.

Figure 3:
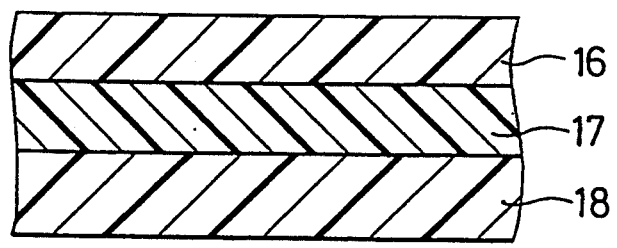
FIG. 3 is a sectional view of a configuration of a multi-layered balloon of the present invention.

PAS and polyolefin pellets may be multi-layered extrusion molded into layers. However, when PAS, a blend of PAS and polyolefin, and polyolefin are molded into three layers as shown in FIG. 3, the PAS layer 18 and the polyolefin layer 16 are preferably adhered to each other with an intermediate layer 17 therebetween. Since the intermediate layer 17 is a non-uniform two-component layer of a blend of PAS and polyolefin, it is impossible to make a clear distinction between the PAS layer 18 and the olefin layer 16. One example of balloons produced by extrusion-molding PPS, a blend of PPS and polyolefin and polyolefin into three layers may have the PPS layer having a thickness of from 5 to 7 $\mu$m, the PPS alloy layer (PPS-polyolefin blend ratio of 1:1) having a thickness of from 1 to 2 $\mu$m, and the polyolefin layer having a thickness of from 5 to 7 μm, with a total thickness of from 11 to 16 μm.

The thus produced balloons of the present invention may have a calculated modulus of elasticity of from 70 to 200 kg/mm$^2$.

A balloon having a calculated modulus of elasticity of less than 70 kg/mm$^2$ is insufficient in strength and dimensional stability. A balloon having a calculated modulus of elasticity in excess of 200 kg/mm$^2$ is insufficient in softness and flexibility leading to poor trackability of the catheter, and easily forms rigid folds, whereby the balloon is easily injured by friction between the balloon and a guiding catheter.

The term, calculated modulus of elasticity, E used herein is determined from a calculated tensile strength, Sc (which represents the tensile strength in radial direction in film equation) shown in the following equation [I].

The pressure-resisting strength of a balloon 3 (see FIG. 1) is determined in a pressure test wherein water is fed into a balloon until is bursts. The pressure-resisting strength is calculated by the following equation known for a membrane.

$$Sc = P \times D / 2t \qquad [I]$$

In the above equation, Sc is pressure-resisting strength of a balloon, which is referred to as a calculated tensile strength of the film; P is the pressure applied to the test sample upon bursting; D is the diameter of the test sample under pressure of 1.0 kg/cm$^2$; and ti is the wall thickness of the test sample. The diameter and the wall thickness of the test sample are determined by observing the cross section of the balloon with a stereoscopic microscope. (See S. Timoshenko, "Strength of Materials", Part II, Second edition, page 165, D. van Nostrand Company Inc., New York, NY, 1941.)

The calculated modulus of elasticity, E corresponds to the slope of the linear portion, wherein Hooke's law is applicable, of the stress-strain curve obtained by plotting the stress component (strength, Sc) in relation to the strain component (inflation of the balloon, D). In other words, the calculated modulus of elasticity is initial modulus of elasticity of the balloon, which may be determined by equation [II]:

$$E = \delta Sc \times D / \delta D \qquad [II]$$

wherein E is the calculated modulus of elasticity, δSc is the calculated tensile strength of the film, D is initial diameter of the balloon, and δD is increment in the balloon diameter.

The balloon of the present invention may have a non-limited thickness, which may preferably be from 5 to 30 μm.

Conventional PET balloons, which are provided with excellent strength and dimensional stability, are quite hard, and have a calculated modulus of elasticity of from 200 to 250 kg/mm$^2$. In the present invention, the calculated modulus of elasticity has been reduced to 70 to 200 kg/mm$^2$, by fabricating the balloon from polyarylenesulfide or the alloy thereof wherein the polyarylenesulfide is a main constituent, whereby a production of a balloon provided with softness and flexibility as well as dimensional stability is enabled.

It is to be noted that the PET balloon could be imparted with a reduced modulus of elasticity by reducing the degree of orientation. In such case, however, in pressure resistance tests for obtaining a calculated modulus of elasticity, the stress-strain curve would exhibit a yield point, beyond which the dimensional stability. Moreover the strength would undergo a significant decrease. A pressurization of the balloon beyond such a yield point would lead to a plastic deformation of the balloon upon which a restoration to its original configuration and dimension would be impossible. Also, this would make the withdrawal or recovery of the balloon difficult. Therefore, only a considerably limited range of pressure may actually be employed for the PET balloon inflation.

In contrast, the balloon of the present invention is provided with sufficient softness and flexibility without compromising the dimensional stability and the strength. Accordingly, the inner surface of the blood vessel to which the blood vessel-dilating catheter is inserted is prevented from being injured by the balloon upon such an occasion as insertion of the catheter.

In addition, the balloon of the present invention has a high glass transition temperature owing to the properties of the material. Further, the balloon is superior in crystallinity and heat resistance, and has an extremely small coefficient of water absorption, excellent chemical resistance and inactivity. Because of these features, the balloon can undergo autoclave sterilization and γ-ray sterilization and does not need to be sterilized with ethylene oxide gas. Therefore, the balloon is well suited for use as a balloon for use in a blood vessel-dilating catheter which may be contacted directly with the blood without fear of hemolysis caused by ethylene oxide gas. Further, it avoid the need to remove the ethylene oxide gas which takes a long time.

The balloon of the present invention will preferably have a burst pressure of 10 kg/cm$^2$ or higher, and more preferably, from 13 to 20 kg/cm$^2$. The pressure normally required for inflating the balloon is approximately 7 to 8 atm. The balloon of the present invention, which has a burst pressure of 10 kg/cm$^2$ or higher, will endure a more severe pressurization than such a normal pressurization, and therefore, may successfully employed for treating a tight stenosis requiring even higher pressurization.

As can be clearly seen by the above description, the balloon comprising the balloon catheter of the present invention is well suited in particular for use in blood vessel-dilating catheters. However, this balloon, given its afore-described properties, comprises many different medical applications, e.g., any application wherein a balloon is to be inserted into a body cavity.

EXAMPLES

Examples of the present invention are described hereunder.

Example 1

Super high molecular weight linear type poly-p-phenylenesulfide (hereinafter abbreviated as PPS) was used as polyarylenesulfide (hereinafter abbreviated as PAS). PPS of grade E0780 manufactured by Toray PPS Co., Ltd. (formerly Toray Phillips Petroleum Co., Ltd.) and having an MFR of 7 [g/10 min] at 316° C. and a melting point of 280° C. was used. The PPS was molded into a tube having an inner diameter of 0.5 mm and an outer diameter of 0.85 mm. The tube was axially oriented to a length 2.5 times larger than its original length in an atmosphere at a temperature of 105° C. The tube was then placed in a metal cylinder provided with a cylindrical cavity with an inner diameter of 3 mm having opposite tapered ends.

The metal cylinder was heated to a temperature of 105° C., and nitrogen gas was introduced into the tube to a pressure of 12 kg/cm² from its opposite ends. The tube was kept at this pressure for 15 seconds. The tube was then allowed to cool to room temperature in 1 minute with the pressure being kept at the constant level.

The metal cylinder was heated again with the pressure being kept at the constant level, but this time to a temperature of 125° C., and the tube was allowed to heat set for 20 seconds and cool to room temperature in 90 seconds.

After reducing the pressure, the biaxially oriented and heated balloon was removed from the metal cylinder, and trimmed to obtain the balloon of the present invention. The resulting balloon had an outer diameter at its dilating portion of 3 mm and a film thickness of 14.3 μm.

Example 2

PPS of grade M2088 manufactured by Toray Phillips Petroleum Co., Ltd. having an MFR of 94 [g/10 min] at 316° C. and a melting point of 280° C. was used. The PPS was molded into a tube having an inner diameter of 0.5 mm and an outer diameter of 0.90 mm. The tube was axially oriented to a length three times larger than its original length in an atmosphere at a temperature of 105° C. The tube was then placed in a metal cylinder provided with a cylindrical cavity with an inner diameter of 3 mm having opposite tapered ends. balloon having an outer diameter at its dilating portion of 3 mm and a film thickness of 15.0 μm was produced in a manner similar to Example 1.

Example 3

A PPS-based polymer blend of grade T-300 manufactured by Kureha Chemical Industry Co., Ltd. was used as a PAS alloy, and a balloon having an outer diameter at its dilating portion of 3 mm and a film thickness of 14.5 μm was produced in a manner similar to Example 2.

Example 4

PPS 10% of which was modified by a meta component (hereinafter abbreviated as M10PPS) was synthesized as a PAS alloy by the following method. That is, 63.6 g (0.5 tool) of sodium sulfate, 123.3 g of N-methyl-2-pyrrolidone and 51.0 g (0.5 mol) of lithium acetate dihydrate were charged into an autoclave while it was stirred. A reaction mixture was produced by heating for 125 minutes and then dehydrated. 31 ml of a distillate containing 27.8 g of water remained after dehydration. When the reaction mixture was heated to a temperature of 205° C., 4.95 g of 4-dichlorobenzene was added to the mixture, and the resultant mixture was kept at a temperature of 245° C. at a gauge pressure in the range of from 4.9 to 7.0 kg/cm² (75 to 100 psi) for three hours. The reaction chamber was then allowed to cool to room temperature to obtain a dark gray product. The product was cleaned with 1 liter of water eight times and dried and synthesized in a vacuum chamber heated to a temperature of 80° C.

The thus produced random copolymer PPS comprises 90% of a paraphenylenesulfide component and 10% of a metaphenylenesulfide component and has a melting point of 253° C. and an MFR of 15 [g/10 min] at 280° C.

The above-described M10PPS was used to produce a balloon having an outer diameter at its dilated portion of 3 mm and a film thickness of 15.3 μm in a manner similar to Example 2.

Example 5

Super high molecular weight linear type poly-p-phenylenesulfide (hereinafter abbreviated as PPS) was used as polyarylenesulfide (hereinafter abbreviated as PAS). PPS of grade E1880 manufactured by Toray PPS Co., Ltd. (formerly Toray Phillips Petroleum Co., Ltd.) and having an MFR of 70 [g/10 min] at 316° C. and a melting point of 280° C. was used. Modified polypropylene (hereinafter abbreviated as MPP) was also used as polyolefin. A polypropylene-based MODIC of grade P-310H out of highly adhesive polyolefin resin commercially available from Mitsubishi Petrochemical Co., Ltd. was used as the MPP.

Three extruders were used to mold a source tube by means of a usually used method. A PPS pellet was used as a source material to form an inner layer, a hand blend pellet having the ratio of PPS to MPP of 1:1 to form an intermediate layer and an MPP pellet to form an outer layer. The thus obtained source tube had an inner diameter of 0.48 mm and an outer diameter of 0.91 mm. The section of the source tube was investigated, but the boundary between the PPS layer and the MPP layer was unclear and it was impossible to peel and separate the PPS layer from the MPP layer.

The tube was axially oriented to a length 3 times larger than its original length in an atmosphere at a temperature of 105° C. The tube was then placed in a metal cylinder provided with a cylindrical cavity with an inner diameter of 2.5 mm having opposite tapered ends.

The metal cylinder was heated to a temperature of 105° C., and nitrogen gas was introduced into the tube to a pressure of 12 kg/cm² from its opposite ends. The tube was kept at this pressure for 15 seconds. The tube was then allowed to cool to room temperature in 90 seconds with the pressure being kept at the constant level. The temperature at this time was 25° C.

The metal cylinder was heated again with the pressure being kept at the constant level, but this time to a temperature of 150° C., and the tube was allowed to cool to room temperature in 110 seconds after the temperature reached 150° C.

After reducing the pressure, the biaxially oriented and heated balloon was removed from the metal cylinder, and trimmed to obtain the balloon of the present invention. The resulting balloon had an outer diameter of 2.29 mm and a film thickness of 16.3 μm when a pressure of 1 kg/cm² was applied. It was impossible to make a distinction between the PSS and MPP layers of the balloon and peel the PPS layer from the MPP layer.

The balloon of the present invention provided the soft touch of polyolefin and had excellent pressure resistance and dimensional stability in spite of high softness.

Comparative Example 1

A commercially PET balloon (having an outer diameter at its dilated portion of 3 mm and a film thickness of 10 μm) was prepared.

Comparative Example 2

A commercially Nylon 12 balloon (having an outer diameter at its dilated portion of 3 mm and a film thickness of 8 μm) was prepared.

Experiment

Figure 2:
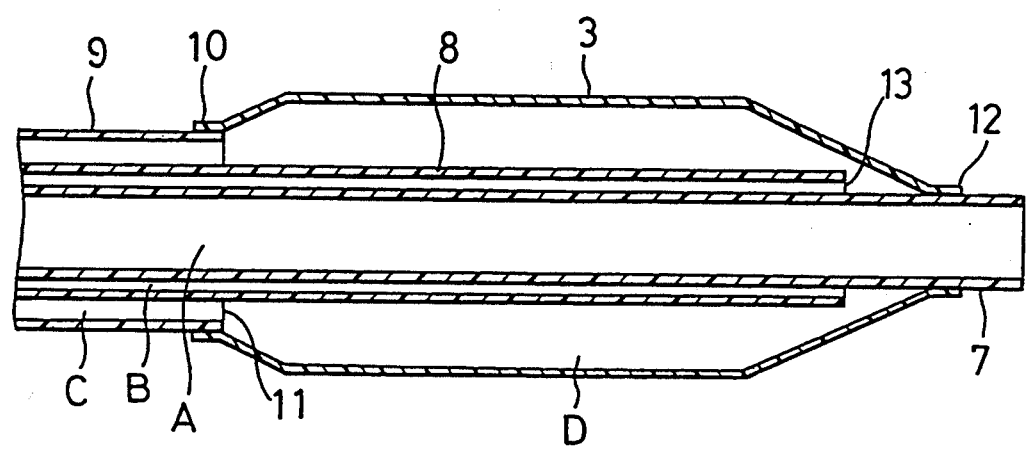
FIG. 2 is a sectional enlarged view of the configuration at a distal end of the blood vessel-dilating catheter provided with the balloon of FIG. 1.

FIG. 1 is a schematic diagram of the configuration of a commercially triple tubular blood vessel-dilating catheter provided with a balloon which was served to experiments. FIG. 2 is a sectional enlarged view of the configuration of the blood vessel-dilating catheter provided with a balloon of FIG. 1.

As shown in FIG. 1, each of the balloon samples obtained in the above-described Examples 1 to 5 and Comparative Examples 1 and 2 was secured by thermal fusion to the outer periphery of the distal end of the tube 2 made of high density polyethylene (HDPE) of the triple tubular blood vessel-dilating catheter 1. Subsequently, distilled water was injected from the injector 6 provided with a pressure gauge connected to the injection port 5 of a three-way adaptor 4 attached to the catheter 1 to charge the balloon 3 with the distilled water. In this case, as shown in FIG. 2, the triple tubular blood vessel-dilating catheter tube 2 comprises an inner tube 7 forming a first passage A and having an open end thereof, an intermediate tube 8 around the inner tube 7 forming a second passage B with the inner tube 7, and an outer tube 9 around the intermediate tube 8 forming a third passage C with the intermediate tube 8. The balloon 3 having a cylindrical portion coaxial with the catheter tube 2 around the triple tubular catheter tube 2 always contains the openings of the second passage B and the third passage C. An end portion 10 of the balloon 3 is secured by thermal fusion to the outer surface of the outer tube 9 at a proximal end thereof away from the side hole 11 of the outer tube 9 and the other end portion 12 of the balloon 3 is secured by thermal fusion to the outer surface of the inner tube 7 at an distal end thereof away from the side hole 13 of the intermediate tube 8 so that a closed space D connected to the second passage B and the third passage C can be formed. (When this triple tubular blood vessel-dilating catheter is actually used as a blood vessel-dilating catheter, the first passage A functions as a passage of blood and the guiding wire 13 (shown in FIG. 1), the second passage B functions as an exhaust passage of residual air, and the third passage C functions as a supply passage of a contrast medium, etc. To the proximal end of the triple tubular catheter tube 2, the three-way adaptor 4 shown in FIG. 1 is attached, and three ports of the three-way adaptor 4 are connected to the respective three passages of the triple tubular catheter tube 2. The guiding wire port 14, the bent port 15 and the injection port 5 of the three-way adaptor 4 are connected to the first passage A, the second passage B and the third passage C, respectively.) Consequently, distilled water was injected from the injector 6 provided with a pressure gauge connected to the injection port 5 to inject the distilled water into the balloon 3 through the third passage C of the triple tubular catheter tube 2, and while the bent port 5 of the three-way adaptor 4 of the other second passage B was closed with a stopper (unshown), pressure was applied to the closed space D of the balloon 3 gradually increasing at a rate of 1 kg/cm$^2$ per minute to conduct a burst test. In this test, the balloon was recorded for its deformation in diameter in relation to the pressure applied.

In this burst test, the balloon was evaluated for its burst pressure and maximum percentage of inflation. In addition, calculated tensile strength and calculated modulus of elasticity were determined from the recorded experimental data by the above-mentioned equations [I] and [II] and the film thickness and initial diameter of the balloon. The results are shown in Table 1, below.

TABLE 1

| | Balloon material | Balloon film thickness (μm) | Calculated tensile strength (kg/mm$^2$) | Calculated modulus of elasticity (kg/mm$^2$) | Burst pressure (kg/cm$^2$) | Maximum inflation (%) |
| --- | --- | --- | --- | --- | --- | --- |
| Ex 1 | PPS E0780 | 14.3 | 19.2 | 177 | 20.0 | 15.8 |
| Ex 2 | PPS M2088 | 15.0 | 17.0 | 189 | 18.1 | 14.2 |
| Ex 3 | PAS blend T-300 | 14.5 | 18.0 | 161 | 19.1 | 12.5 |
| Ex 4 | PAS copolymer M10PPS | 15.3 | 16.1 | 127 | 18.0 | 16.1 |
| Ex 5 | PPS/MPP | 16.3 | 11.9 | 75 | 17.4 | 10.2 |
| CEx 1 | PET | 10.0 | 29.1 | 232 | 20.0 | 13.4 |
| CEx 2 | N12 | 8.0 | 15.3 | 43.9 | 9.0 | 32.4 |

The data in Table 1 reveal that the balloon of the invention produced in Examples 1 to 5 had a calculated modulus of elasticity in the range of from 70 to 200 kg/mm$^2$, and a burst pressure of as high as over 10 kg/cm$^2$ to exhibit sufficient dimensional stability as well as satisfactory softness and flexibility.

In contrast, the balloon of Comparative Example 1 had a calculated modulus of elasticity of as high as 232 kg/mm$^2$, and as the results of measurement, samples of various PET balloons had a calculated modulus of elasticity in the range of from 200 to 250 kg/mm$^2$. Owing to such a high modulus of elasticity, the PET balloon exhibited poor flexibility.

In order to reduce the modulus of elasticity, a sample with a reduced degree of orientation was prepared by repeating the procedure of Example 1 except that a PET tube was employed, the orientation temperature was set at 85° C., and the degree of axial orientation was reduced to 2.67. The resulting balloon had an outer diameter at its dilated portion of 3 mm and a film thickness of 15.5 μm.

The thus prepared balloon was subjected to the abovedescribed burst test. The balloon had a calculated tensile strength of 16.8 kg/mm$^2$ and a calculated modulus of elasticity of 130 kg/mm$^2$. The burst pressure was 18.2 kg/cm$^2$ and the maximum inflation rate was 22.5%.

The balloon, however, exhibited a yield point in stress-strain curve. When a balloon compliance, namely, the balloon diameter in relation to the pressure was measured, a significant increase in the balloon diameter was observed at a pressure of 10 kg/cm² to show that the balloon had undergone a plastic deformation after the yield point. Indeed, the balloon failed to restore its original dimension after the lowering of the pressure.

As described above, the modulus of elasticity may be reduced by such means as adjusting the degree of orientation. The resulting balloon, however, is not desirable for the purpose of the present invention since it exhibits a yield point and a pressure actually used is inevitably a level lower than the yield point. The balloon which has undergone a plastic deformation in a living body not only fails to restore its original shell dimension at the time of recovery but also disrupts into the flap configuration with ease, thus making it difficult to pass the guiding catheter therethrough and recover the balloon, which is not preferable.

The balloon of Comparative Example 2 had a low calculated modulus of elasticity of 43.9 kg/mm², and accordingly, a burst pressure of as low as 9.0 kg/cm². The pressure normally required for inflating the balloon is approximately 7 to 8 atm. Some operators, however, may conduct balloon inflation at a pressure of approximately 10 atm. or even higher. A burst pressure of less than 10 kg/cm² would therefore be insufficient.

The mode of the burst pressure of the balloon is also a matter of interest. The balloons of Examples 1 to 4 of the present invention were axially split upon bursting, and therefore, could easily be recovered. In contrast, some PET balloon having a high modulus of elasticity bursted into numerous debris, which were quite difficult to recover if not impossible.

If such a bursting of the balloon should take place in a living body to leave unrecoverable balloon debris in the blood vessel, they may induce an extremely dangerous clogging in coronary artery as well as peripheral blood vessels. The balloon of the present invention undergo a bursting wherein a woolly residuum is left. The balloon of the present invention, therefore, could be thoroughly recovered with no significant difficulty even if the balloon should burst in a living body.

As set forth above, the balloon of the present invention for a balloon catheter is provided with excellent dimensional stability as well as sufficient softness and flexibility, leading to an improved trackability of the catheter to reach the target lesion. Injury of the blood vessel upon the introduction of the catheter into the blood vessel is also prevented.

The balloon of the present invention also has an improved adhesibility to the catheter to which the balloon is secured. This is quite advantageous in structure, and peeling of the balloon from the catheter is avoided.

Furthermore, the balloon of the present invention could easily be subjected to various surface treatments including coating of anti-thrombotic materials and agents on the exterior surface of the balloon.

Still further, the balloon of the present invention has a high burst pressure and a low modulus of elasticity as well as an excellent impact strength to fully endure a rapid ballooning or inflation at a high pressure. Therefore, the balloon of the present invention is quite safe.

Moreover, the balloon of the present invention has sufficient heat resistance and chemical resistance inherent to the material thereof, and is water absorptive. Therefore, it can be subjected to sterilization such as autoclave sterilization and γ-ray sterilization, leading to improved safety and operation efficiency.

What is claimed is

1. In a balloon catheter having an inflatable balloon, the improvement comprising: the balloon produced by molding a polyarylenesulfide or an alloy thereof wherein the polyarylenesulfide is a main constituent.

2. The improvement according to claim 1, wherein said balloon is fabricated by multi-layered extrusion molding using at least two materials selected from the group consisting of polyarylenesulfide, an alloy thereof, olefin polymer, an alloy thereof, and mixtures thereof.

3. The improvement according to claim 1, wherein said polyarylenesulfide is at least one selected from the group consisting of polyphenylenesulfide, polythioether ketone, polythioether thioether ketone, polythioether ketone ketone, polyether thioether, polythioether sulfone, polybiphenylene sulfide and polynaphthalene sulfide.

4. The improvement according to claim 1, wherein said polyarylenesulfide is a high molecular weight polyphenylenesulfide.

5. The improvement according to claim 1, wherein said balloon has a calculated modulus of elasticity of from 70 to 200 kg/mm².

6. The improvement according to claim 1, wherein said balloon has a burst pressure of at least 10 kg/cm².

7. The improvement according to claim 1, wherein said balloon has a film oriented biaxially.

* * * * *